US009653258B2

(12) United States Patent
Grzelakowski

(10) Patent No.: US 9,653,258 B2
(45) Date of Patent: May 16, 2017

(54) NEAR-FIELD OPTICAL TRANSMISSION ELECTRON EMISSION MICROSCOPE

(71) Applicant: Krzysztof Grzelakowski, Wroclaw (PL)

(72) Inventor: Krzysztof Grzelakowski, Wroclaw (PL)

( * ) Notice: Subject to any disclaimer, the term of this patent is extended or adjusted under 35 U.S.C. 154(b) by 0 days.

(21) Appl. No.: 15/049,024

(22) Filed: Feb. 20, 2016

(65) Prior Publication Data

US 2016/0254120 A1    Sep. 1, 2016

(30) Foreign Application Priority Data

Feb. 26, 2015    (PL) .......................................... 411407

(51) Int. Cl.
| | |
|---|---|
| *H01J 37/26* | (2006.01) |
| *H01J 37/285* | (2006.01) |
| *H01J 37/20* | (2006.01) |
| *H01J 37/22* | (2006.01) |

(52) U.S. Cl.
CPC ............ *H01J 37/285* (2013.01); *H01J 37/20* (2013.01); *H01J 37/22* (2013.01); *H01J 2237/2007* (2013.01); *H01J 2237/2855* (2013.01)

(58) Field of Classification Search
USPC ................ 250/305, 306, 307, 309, 310, 311, 250/440.11, 441.11, 442.11, 443.1; 850/8, 9

See application file for complete search history.

(56) References Cited

U.S. PATENT DOCUMENTS

| | | | |
|---|---|---|---|
| 2004/0159787 A1* | 8/2004 | Nakasuji | ................. H01J 37/28 250/311 |
| 2012/0235036 A1* | 9/2012 | Hatakeyama | ...... G01N 23/2251 250/310 |

* cited by examiner

*Primary Examiner* — Nicole Ippolito
(74) *Attorney, Agent, or Firm* — Michael Soderman

(57) ABSTRACT

The Near-field Optical Transmission Electron Emission Microscope involves the combination, in one instrument, of optical imaging in the near-field regime or close to it (in respect to the transmission electromagnetic radiation when the wavelength exceeds the desired lateral resolution) and the secondary electron imaging of EEM microscope ("Cathode lens objective" based Emission Electron Microscopy). These two microscopic techniques are combined by the application of the photon-electron converter, which converts the optical, transmission image of the object (illuminated by the penetrating electromagnetic radiation) to the correlated photoelectron image, by means of a matrix of one-way closed channels (capillaries). The closed, smooth front face of the converter (comprising channel-bottoms) remains in contact with the object of imaging, whereas its opposite, opened face (consisting of an array (matrix) of channel openings) is exposed to vacuum and emits the secondary electrons.

11 Claims, 3 Drawing Sheets

NEAR-FIELD OPTICAL TRANSMISSION ELECTRON EMISSION MICROSCOPE

CROSS REFERENCE TO RELATED APPLICATIONS

This application claims the priority of Polish Application No. P.411407 filed on Feb. 26, 2015; this application is incorporated by reference herein in its entirety.

BACKGROUND

The subject of the invention is the Near Field Optical Transmission Electron Emission Microscope, abbreviated NOTEM: an analytical imaging instrument dedicated to optical object inspection and observation with transmission electromagnetic radiation, that utilizes (for imaging, magnification and detection of the original photon transmission image) the secondary electrons generated by this image.

In its principle of operation, function and applications, the subject of invention concerns the area of investigation and imaging of:

1) objects in any physical state, located under vacuum as well as in the gas atmosphere under arbitrary pressure (also under overpressure), including insulators, semiconductors, conductors and superconductors, dielectrics, ferroelectrics, piezoelectrics, paraelectrics, diamagnetics, paramagnetics, ferromagnetics, ferrimagnetics, antiferromagnetics, chemical compounds and substances, minerals, organic and inorganic matter, living and nonliving matter, i.e. any biological material(also in vivo in its natural environment or exposed to any gas atmosphere) or fluids and p 2) processes (occurring in the above-mentioned objects), e.g. physical, chemical, physicochemical, electrochemical, temperature dependent, magnetic, electrical, etc. (also in real time), with secondary electrons generated as a result of conversion of the object penetrating electromagnetic radiation, non-polarized or polarized linearly, circularly/elliptically, e.g.: synchrotron radiation, X-Ray, laser light, UV-light or visible light, etc.

The terms "photon" and "electron" occurring in the nomenclature of the subject of invention: "Near-field Optical Transmission Electron Emission Microscope" determine its simultaneous relationship to the two wide fields of imaging techniques: optical and electron microscopy.

Concerning the character of the photon interaction with the object of imaging in the context of the invention, the first of the afore mentioned fields of microscopy, namely the optical, will be reduced to the aspects of the near-field approximation only, originally described by E. H. Synge in 1928 and experimentally realized by E. Betzig et al.: "Breaking the diffraction barrier optical microscopy on a nanometric scale", Science 251 (1991) 1468.

On the other hand, the object of invention in its electronoptical part belongs to the emissions- and transmissions-electron microscopy techniques utilizing 'parallel imaging', which is an intrinsic feature of the cathode lens objective, invented by E. Brueche in 1932 and developed by E. Bauer: "Cathode lens electron microscopy: past and future", J. Phys.: Condens. Matter 21 (2009) 314.

The principle of optical imaging in the near-field regime has been originally applied in the Scanning Near-field Optical Microscope (SNOM), in which the light source, i.e. an optical fiber tip, is moved close above the object's surface at a distance shorter than the photon's wavelength, resulting in the lower lateral resolution.

The invention's utilization of the principle of the conversion of the transmission optical image into a correlated emission electron image in the object plane of the cathode lens objective determines its relation with the two types of electron microscopy: 1) TEM—Transmission Electron Microscopy and 2)EEM—Emission Electron Microscopy (PEEM—Photoemission Electron Microscopy, LEEM—Low Energy Electron Microscope).

In the Transmission Electron Microscopy TEM developed by Ernst Ruska in 1933, the object of imaging(a transparent foil) will be penetrated by the high energy electron beam, which implies its localization under vacuum: "Transmission Electron Microscopy", D. B. Williams and C. B. Carter, 2009.

Because the penetration depth of the X-Ray in matter is significantly higher than the penetration depth of electrons, only the former (also a synchrotron radiation) has been utilized in many further instrumental developments of Transmission Optical Microscopy: "Projection X-Ray Microscopy" (Newberry, 1954), "Imaging X-Ray Microscopy" (Rudolf et al., 1984), "Scanning X-Ray Microscopy" (Horowitz and Howell, 1972) and "Contact Imaging" (Goby, 1913).

Since its introduction at the "Symposium on X-ray Microscopy and Microradiography" in 1956 by G. Möllenstedt and L. Y. Huang, followed by their article "Röntgen-Bildwandler-Mikroskopie" published in the next year in Zeitschrift für Physik, 149 1957 p. 225, the original concept of the conversion of the transmission optical image to the photoelectron image developed in the Institute of Physics of Gottfried Moellenstedt, has been the subject of many subsequent instrumental realizations.

A representative example of further developments is described in the article of F. Polack and S. Lowenthal in "Journal de Physique, Colloque C2, suppl. no. 2, Tome 45, Fevr. 84, 1984, p. c2-73", which initiates the new class of electron microscopy: "Photoelectron X-Ray Microscopy".

In their version of the transmission microscope the homogeneous, smooth and structureless 100 nm-500 nm thin kapton foil (used as an object holder) has been covered on the vacuum side by a photoemissive material in order to convert photons to electrons.

A further improvement from 1988, presented in the report: "First Images with the Soft X-Ray Image Converting Microscope at LURE"/X-Ray Microscopy II, *Springer Series in Optical Sciences* 56 1988 220, has resulted in the application of cesium covered gold foil instead of the previously used kapton foil.

Another version of the Photoemission Electron Microscope invented by H. Hirose in 1990 is known from the U.S. Pat. No. 5,045,696, in which an analyzed object is held by a holder that consists of a support silicon membrane (on the object side) and a photocathode layer attached to the opposite membrane surface (on the vacuum side).

In this realization the earlier applied kapton or gold foil has been replaced by a 100 nm thin, homogeneous, smooth and structureless doped silicon membrane as an object holder (covered on the vacuum side by cesium iodide) that separates the vacuum part of the instrument from the atmospheric air and is surrounded by the magnetic coil and equipped with a grid electrode in order to generate a photoelectron image.

In the subsequent concept of Sh. Ohsuka et al. from 1990 entitled: "X-ray image observing device" and published in U.S. Pat. No. 4,912,737, the X-Ray transmission microscope has been equipped with the magnetic lens system only (without any electrostatic extractor field).

After transmission through the investigated object and its homogenous, smooth and structureless holder membrane, the divergent X-Ray radiation enters the vacuum area at the photocathode layer, where the optical image evolves and the photoelectric process takes place, resulting in the conversion to the photoelectron image.

This image will be further magnified with the magnetic lens system (without an application of the electrostatic extractor field) and projected on the fluorescence screen.

Another version of the optical transmission electron microscope invented by Bi Yu in 2005 is known from the U.S. Pat. No. 7,006,741, in which the fiber optic taper has been adapted to convert the optical image into the photoelectron image.

In lieu of the homogenous, smooth and structureless object-holder membrane, a massive optical element constructed from a number of glass fibers in the form of a cone has been applied, with the narrow face exposed to the investigated object and the wide face covered by a photoemissive layer exposed to vacuum.

The photons of the magnified (by the fiber optic geometry) optical image generate, as a result of the photoelectric effect in this layer, a photoelectron image on the vacuum side.

The above-mentioned realizations have been extended in 2006 by S. Fujii et al. in a "X-Ray Microscope Apparatus" by the three aspects reported in the U.S. Pat. No. 7,039,157: a) an integrated X-Ray laser source, b) the electrostatic component of the field around the photocathode/object and c) a tilted image detector (referred to the radiation axis).

The second technology area that is relevant to the subject of invention refers to the Electron Microscopy based on the cathode lens objective (immersion objective): 1) E. Bauer'a: "Surface Microscopy with Low energy Electrons", Springer Verlag, 2014, and 2) O. H. Grifith's and W. Engel's, "Historical perspective and current trends in emission microscopy, mirror electron microscopy and low energy electron microscopy", Ultramicroscopy 36 (1991).

The advantage of the "cathode lens objective" based electron microscopy has been confirmed in many instrumental realizations: in the case of photoelectrons as a PEEM (Photoemission Electron Microscopy)—E. Brüche, in the case of slow electrons as a LEEM (Low Energy Electron Microscopy)—E. Bauer and SPLEEM (Spin Polarized LEEM)—K. Grzelakowski et al., JEEE Transactions on Magnetics, 30 6 (1994), as well as DEEM (Dual Emission Electron Microscope): K. Grzelakowski, *Ultramicroscopy* 130 (2013) 29.

Such a "cathode lens objective"—based PEEM (Photoemission Electron Microscope) with the transmission photon-electron image conversion has been reported in 1997 by R. N. Watts et al. in Rev. Sci. Instrum. 68 (1997) 3464 as a "High Resolution Image Converter For Soft X-Ray Microscopy", which utilizes the earlier idea of the homogenous, smooth and structureless silicon nitride membrane covered (on the vacuum side) by the carbon buffer layer and cesium iodide as a photocathode.

Another analogous realization of the idea and its application is known as the X-Ray Transmission Electron Microscope from two publications of G. De Stasio et al., respectively: Rev. Sci. Instrum. 69 (1998) 3106 and Rev. Sci. Instrum., 71 (2000) 11.

Also the biological applications of the Photon Transmission Electron Microscope in the investigation of the copper nanoparticles in protein KLH1 are known, published by D. Panzer et al. in Eur. Biophys. J 38 (2008) 53: "Transmission photoemission electron microscopy for lateral mapping of the X-ray absorption structure of a metaloprotein in a liquid cell".

A further electron microscopy area that is relevant to the subject of invention, refers to the object inspection of integrated circuits in lithographic techniques.

Such a mask inspection instrumentation for the imaging of the lithographic mask described in U.S. Pat. No. 6,002,740 by F. Cerrina and T. B. Lucatorto is based on the integration of the PEEM microscope into the production line just above the lithographic mask that is illuminated from the opposite side by X-Ray radiation.

Similar to the former solutions, the photon-electron converter consists of the photocathode as a phosphor-cesium iodide layer evaporated onto the homogenous, smooth and structureless 100 nm thin silicon nitride membrane.

A further instrumental realization in the field of photon transmission electron microscopy: "X-ray photoemission microscope for integrated devices", which was also dedicated to the inspection of an integrated circuits, has been presented in 2014 by D. L. Adler in the US patent application No. 20140037052.

In this case the X-Ray radiation penetrates the inspected integrated device located outside the vacuum, propagating towards the homogenous, smooth and structureless converter inside the vacuum, separated from the object by the X-Ray transparent window.

Another variation of Adler's concept adapts the converter geometry of H. Hirose from 1990 (U.S. Pat. No. 5,045,696); however, the object of imaging is located on the air side, which enables its shift and adjustment.

In a further variation of his concept, D. L. Adler has proposed using homogenous and structureless beryllium-or diamond photocathode in lieu of the previous Hirose's silicon nitride photocathode membrane.

In the third variation, the photocathode has been evaporated directly onto the inspected integrated device.

SUMMARY

The subject of invention: Near-field Optical Transmission Electron Emission Microscope refers to the combining in an instrument of optical imaging in the near-field regime or close to it (in respect to the transmission electromagnetic radiation when the wavelength exceeds the desired lateral resolution) and the secondary electron imaging of EEM microscope ("Cathode lens objective" based Emission Electron Microscopy).

The combining of these two microscopic techniques is performed by the application of the photon-electron converter, which converts the optical, transmission image of the object (illuminated by the penetrating electromagnetic radiation) to the correlated photoelectron image, by means of a matrix of one-way closed channels (capillaries).

The closed, smooth front face of the converter (comprising channel-bottoms) remains in contact with the object of imaging, whereas its opposite, opened face (consisting of an array (matrix) of channel openings) is exposed to vacuum and emits the secondary electrons.

In the invention, the secondary electrons emitted from the matrix of channel openings towards the vacuum create an image, which is proportional to the transmission optical image.

The converter membrane (and basically the matrix of the channel openings in the converter's face) is located in the object plane of the cathode lens objective (immersion lens) and acts in this plane as an intermediate object created proportionally to the original transmission optical image by means of the secondary electrons emitted from the channel openings.

In the NOTEM the potential of the first electrode of the cathode lens objective on the side of the converter is positive with respect to the potential of the converter's face.

DETAILED DESCRIPTION

The essence of invention of the Near-field Optical Transmission Electron Emission Microscope in the context of optical microscopy and its near-field regime, manifests itself in these different aspects:

a) in the illumination of the investigated object (under arbitrary angle α: 0≤α≤90°) with electromagnetic radiation, e.g. synchrotron light, X-Ray, laser light, UV—or visible light, non-polarized or polarized linearly or circularly/elliptically, etc., (preferably with homogenous, parallel beam/beams or convergent (scanning), divergent (wide field illumination) or collimated beam/beams), b) in the optical (or/and mechanical) contact between the investigated object (and its transmission photon image) with the structure of the preferably parallel channels (capillaries) of the converter membrane/object holder (oriented along the electronoptical axis or under an arbitrary angle β: 0≤β≤90°), through the buffer separation layer or multilayer (because of the near-field regime preferably thinner than the wavelength), on the one hand transparent (or partially transparent) for the illumination electromagnetic radiation, on the other hand hermetic for the particles, in order to establish a mechanical or/and vacuum stable barrier between the object and the vacuum-exposed interior of channels, and c) in the penetration of the 2D photon yield (i.e. photon image weighted by the specific, optical absorption or/and optical scattering in the object) into the vacuum-exposed interior of the channels, through their closed ends (bottoms) and/or a buffer layer (or multilayer), where the photoelectrons and/or secondary electrons will be generated.

In this context, referring to the wavelength of the object penetrating radiation, the channel's separation "d" determines the lateral resolution "r" of the photon-electron image converter, and the channel's diameters its transmittance.

In accordance with the invention, the transmission of the electromagnetic radiation through the investigated object results in the formation of the optical image as a 2D intensity distribution in the interface contact plane between the object and the electromagnetically transparent channel bottoms (and/or the buffer layer or multilayer), which simultaneously separates the object from the channel's interiors located in vacuum.

Consequently, after transmission of the illuminating radiation through the investigated object and creation of an optical image, its photons penetrate the transparent (or partially transparent) channel bottoms (and/or separation layer or multilayer) and finally interact with their photoemissive surface on the vacuum side.

In this photoemissive layer a photoelectric effect takes place, which converts the transmission optical image (established by the matter-dependent photon absorption and/or scattering in the investigated object) into the correlated two dimensional photoelectron intensity distribution, unless the photon energy overcomes the work function.

If the wavelength of the object penetrating electromagnetic radiation exceeds the desired lateral resolution, the photon-electron image conversion will be preferably realized in the near-field regime (Fresnel diffraction limit) or close to it (between Fresnel and Fraunhofer approximation).

In this context the thickness of the closed channel ends (channel's bottoms) and/or separation layer/multilayer as well as the channel's distance referred to the wavelength determine the influence of the optical diffraction on the final lateral resolution.

After the conversion of photons to correlated electron image is completed, all subsequent optical phenomena undergo the rules of the electron optics in the far-field approximation.

The essence of invention of the Near-field Optical Transmission Electron Emission Microscope lies in its utilizing for the final imaging not only photons but additionally secondary electrons, which are generated in the interiors of the one-way closed (on the object side) converter's channels in vacuum and subsequently, after the emission from the matrix of opened channel ends as an intermediate object (located in the object plane of the cathode lens objective), create a final electron image by means of the integrated converter-cathode lens geometry.

Such an electronoptical geometry, in which according to the invention the photon-electron converter is integrated with the cathode lens objective, results in the penetration of the objective's extractor field into the channel's interiors and subsequently, in the acceleration of the emitted secondary electrons proportionally to the photon yield as a result of the successive collisions with the channel's surface (preferably with secondary emission coefficient >1).

In the first stage the extractor field accelerates the photoelectrons that are excited through photoelectric effect in the photoemissive channel's closed ends/bottoms (and/or in layer or multilayer of the closed channel's closed ends/bottoms) in the channel's interior.

Facilitated by the preferably small channel diameter e.g. from ~1 nm-10 nm (in the case of nanotubes) and ~10-~100 nm (in the case of ceramics) to a few hundreds of nanometers (in the case of other materials) the photoelectrons collide with the emissive channel's walls and generate a multiple emission of the secondary electrons, especially if the channel's surface exhibits the secondary emission coefficient >1.

The field inside the channels facilitates the acceleration of the electron cloud up to the next collision with the emissive channel wall, resulting in the signal's amplification.

This cascade like process continues, till the secondary electrons leave finally the 2D-arrangement of channels (through the channel openings), leading to the grating (rastering) of the original near-field optical image, in the form of the electron intensity matrix (located on the vacuum side in the object plane of the cathode lens objective), which operates as an intermediate object/cathode used now for the imaging and magnification with the electron-optical system.

Ergo the raster-like secondary electron image that proportional to the optical image (generated after transmission of the electromagnetic radiation through the object) and acts as an intermediate object for the cathode lens objective, will be projected either direct on the image detector or at the input to the electronoptical system.

One distinctive attribute of the invention is also the enhancement of the accelerating electrostatic field, penetrating the interior of the converter's channels, by applying the coinciding with this field additional voltage, on the one hand to the channel's closed ends/bottoms (lower potential) and on the other hand to the front face of the array (matrix) of channel's openings (higher voltage)—either directly or with the contact electrodes.

According to the invention, the resistance of the channel's surface results in the formation of the potential distribution in the channel's interiors and finally, in the additional contribution to the accelerating field: ~U/I (U—voltage, I channel length), what enables the desired enhancement of the secondary electron yield at the channel's openings.

The Near-field Optical Transmission Electron Emission Microscope as described consists at least of an electronoptical, object magnifying lens, an object illuminating/penetrating electromagnetic radiation system, an electron image detector (e.g. 2D image intensifier with fluorescent screen or 2D electron detector, e.g. delay line detector, etc.), an object holder/object manipulator, e.g. equipped with heating/cooling system (either only XY, XYZ or optionally object's tilt $\ominus$) optional with the manipulation system for the in (ex) situ influencing of the object on the micro or/and sub-micro scale, and finally the housing/vacuum chamber, which enables as well the pumping down of the converter's channels and the electron-optics part as the gas dosage or evaporation (coating) in order to achieve surface activation.

Another characteristic attribute of the invention is the enclosing of the investigated object in an additional hermetic chamber (independent of the vacuum of the electron-optics part), which is equipped with the pump system and/or with the dosage system of gases under an arbitrary pressure and/or with the evaporation/coating system.

According to the invention, around the investigated object kept at the arbitrary temperature, either a vacuum, gas atmosphere or fluid in the desired chemical composition will be applied.

Furthermore, according to the invention, the investigated object will be illuminated and/or penetrated by the electromagnetic radiation, e.g. with X-Ray, light (in general), UV-light, laser light, etc., shaped in the context of: a) tilt angle and/or b) energy spectrum (e.g. wide emission spectrum or monochromatic or a combination of monochromatic beams) and/or c) angular distribution (convergent, divergent or collimated beam) and/or d) polarization mode.

The characteristic attribute of the invention is due in this context to the object penetration/illumination with one (or multiple) beam/beams of the electromagnetic radiation/radiations, linearly, circularly, elliptically, azimuthal, radial, vortex-like or non polarized beam/beams in order to evoke the contrast: magnetic, electric, chemical, physical, fluorescent, radioactive, density, phase, material state, exciting state, etc.

According to the invention, the object illuminating/penetrating electromagnetic radiation (e.g. synchrotron light, X-Ray, laser light, light (in general), UV-light, etc.) is tilted to the converter's channels under the arbitrary angle $\alpha$: $0 \leq \alpha \leq 90°$, whereat the pivot point of the radiation direction preferably coincides with the image center of the object.

In the invention, the investigated object is exposed (in the real time of observation or before) to arbitrary modifications: e.g. in gases or/and fluids, mechanical (visualization of the mechanical stress), chemical (visualization of the chemical reactions), physical, electrical, magnetic, electrolytic, temperature (heating/cooling), current, layer growth (epitaxie, evaporation), diffusion, catalysis, segregation, adsorption, desorption, corrosion, phase transitions, plasma discharge, exciting processes, lithography, etc.

Although some of the observations of the object and its processes can be carried out in the air atmosphere, the majority of the earlier mentioned phenomena require either vacuum and/or dedicated gas atmosphere, and therefore the enclosing of the object in the hermetic chamber.

The characteristic attribute of the invention is due also to the exposing of the object (during the observation or before) to the external fields: e.g. magnetic or/and electrostatic.

DETAILED DESCRIPTION OF THE PREFERRED EMBODIMENTS

Figure 1:
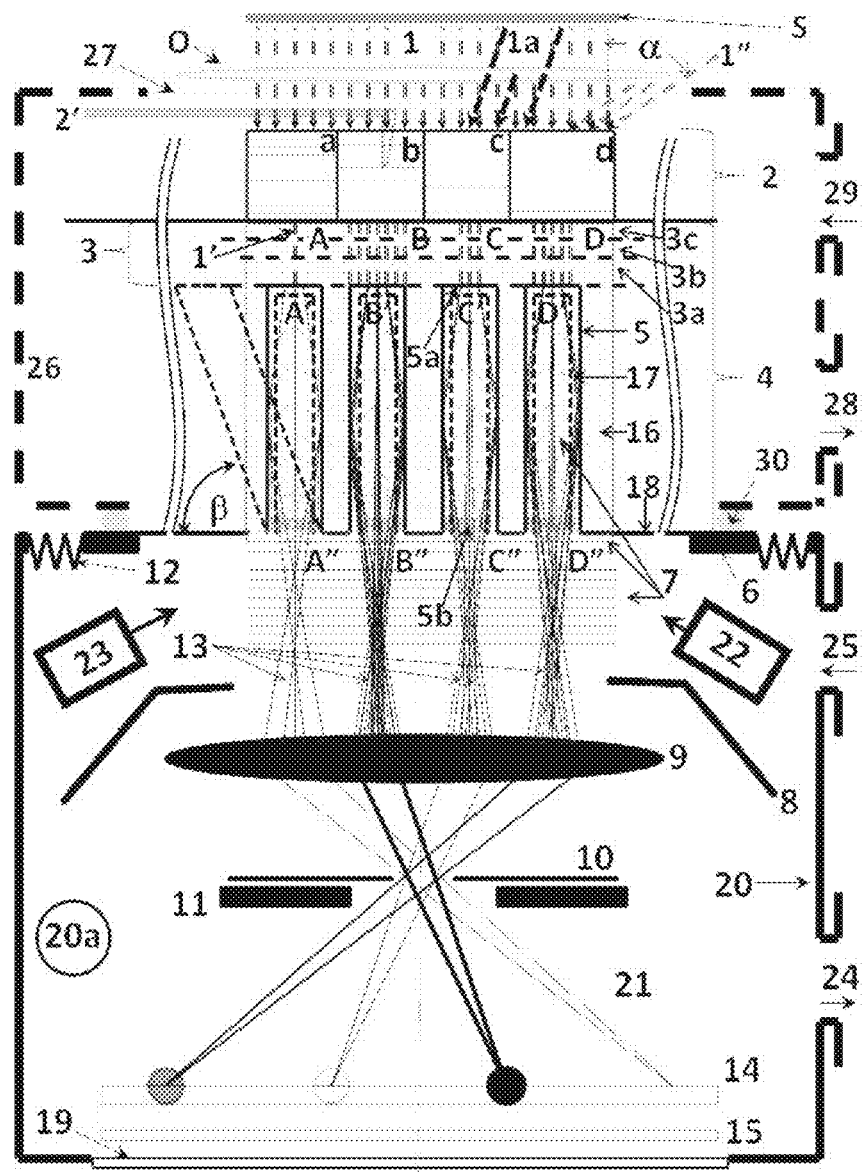
FIG. 1 illustrates the object of invention: the Near-field Optical Transmission Electron Emission Microscope (NOTEM) and its conversion method of the transmission optical image to the secondary electron image by means of the integrated with cathode lens objective photon-electron multichannel converter (for electron converting, intensifying and grating (raster) of the transmission optical image), as well as the schematic (not to scale) presentation of the basic components of the NOTEM microscopes: 1) the multichannel converter/object holder module for the photon-photoelectron-secondary electron conversion under several aspects of realization examples, equipped with the electromagnetic, object penetrating radiation system, 2) cathode lens objective (electrostatic or magnetic) with stigmator and contrast aperture, 3) electronoptical imaging system, 4) electron image detector and schematically illustrated secondary electron trajectories.

FIG. 1 illustrates in the presented example of realization of the subject of invention either the Near-field Optical Transmission Electron Emission Microscope (NOTEM) itself, as its photo-electron conversion method of the transmission optical image into the secondary electron image under several aspects of the multistage image creation process: 1) generation of the transmission optical image (denoted as ABED) at the output of the object's 2 elements abcd, and 2)formation of the photoelectron image A'B'C'D' at the photoemissive surface of the closed ends (bottoms) 5a of the channels 5 of the converter 4 after transmission of the optical image ABCD to this surface on the vacuum side, and 3)creation of the electron image A"B"C"D" by the secondary electrons 13 generated in the channel's 5 interior at, that leave the matrix of the channel's openings 5b as an array of electron intensities (raster electron image A"B"C"D") in the object plane 18 of the cathode lens objective 8,9.

This final 2D array of electron intensities A"B"C"D" is correlated to the investigated object 2 (abcd), as a result of the material/structure dependent absorption-or/and scattering mechanisms of the radiation's photons 1,1a,1" in the object 2 (abcd) and the proportional photon-electron conversion (ABCD→A'B'C'D'→A"B"C"D"), and can be now set as an intermediate object for the imaging with the cathode lens objective 8,9,9',9".

In order to arrange all basic elements of the invention's subject in one figure, they are presented in FIG. 1 not to scale.

The subject of invention, the Near-field Optical Transmission Electron Emission Microscope (NOTEM) operates in the all examples of realization in the photon-optical part of the NOTEM microscope, preferably in the regime of near-field (Fresnel's diffraction limit: near-field zone) or in its vicinity (in the intermediate-field zone between Fresnel and Fraunhofer limit), if the wavelength of the object 2 penetrating, electromagnetic radiation 1,1a,1" the dimensions of the investigated object's elements abcd exceeds. This relationship results in the converter's 4 thickness in the sub-micrometric, or even nanometric range, whereat the continued with electrons imaging in the electronoptical in-vacuum part (i.e. 8,9,9',9",10,14,15,21)of the Near-field Optical Transmission Electron Emission Microscope (NOTEM) microscope is realized on the macroscopic scale.

The near-field regime will be less rigorous in the case of the electromagnetic radiation 1,1a,1" with the wavelength smaller than the lateral resolution, e.g. in the classical optical microscopy.

After the imaging of the investigated object 2 with photons of the electromagnetic radiation 1,1a,1' and after the photon-electron conversion in the near-field regime, the subsequent imaging in vacuum 20a will be carried out in the far-field regime with secondary electrons 13, that are in the emissive interior of the converter's channels 5 generated with the wavelength several orders of magnitude smaller than the wavelength of the object penetrating radiation 1,1a,1'.

Therefore this new electron diffraction limit (referred to the extremely short electron wavelength) does not endanger the original, optical lateral near-field resolution and contrast, even in the situation of the close-packed channel matrix A'B'C'D' of the converter 4 (e.g. ~$10^4/\mu m^2$, at the channel's separation ≈10 nm). In the illustrated in FIG. 1 example of realization of the NOTEM microscope, the typical lateral electron resolution of the cathode lens objective 8,9 and electronoptical system 21 equals a few nanometers.

Though every component necessary to build and to operate the Near-field Optical Transmission Electron Emission Microscope (NOTEM) is correctly indicated in FIG. 1, the microscope on the whole is not drawn to scale.

In this general example of the realization illustrated in FIG. 1 several options and variants of the concept of near field photon-electron conversion are indicated and considered under the following aspects: 1)different kinds of the object 2 penetrating electromagnetic radiation 1,1a,1", as well as the arbitrary angle of slope (indicated in the example of radiation 1"), 2)electromagnetic illumination or/and object 2 penetration from one or more sources S (e.g. radiation 1 or/and 1a, successive or simultaneously), in order to excite the chemical components or/and to enhance the image contrast, 3)optional application of the mechanical-optical system O in order to arrange the beams of the electromagnetic radiation 1,1a,1" in the sense of their form and orientation, of the phase, of the spectrum or polarization, 4)different types of the cathode lens objective 8,9: electrostatic or/and magnetic, 5)different geometry and structure of the channels 5 of the converter 4. 6)optional manipulator 6 for the XY shift and or/and angular adjustment of the object 2 (referred to the electronoptical axis), 7)optional, hermetic vacuum-or/and gas chamber 26 for the encapsulation of the object 2, 8)optional, the micro-manipulation system 2' for the realization of the high-precision, sub-micrometric object modifications before or in real time during the observation.

For the sake of simplicity only the most characteristic configurations will be discussed in the selected examples of realization of the invention's subject.

As a starting point, according to the FIG. 1 the configuration of the cathode lens objective 8,9 together with the integrated multichannel converter will be considered.

The configuration of the channels 5 is in fact arbitrary, however the structures (in the sense of the symmetry group) that result in the ordered and regular array (matrix) of the openings 5b of the converter's channels 5 and in the similar or identical channel density (i.e. lateral resolution) in both vertical directions, e.g.: quadratic, centered, hexagonal (the highest transmissivity), etc., will be favored.

The choice of the grating constant d of the array structure (matrix) of the channel's openings 5b is dictated by the diffraction limits (near-field approximation) of the object penetrating radiation 1,1a,1", that are also determined as well by the thickness of the closed channel ends (bottoms) 5a and/or the layer (multilayer) 3: from several to several hundreds of nanometers, as by the current wavelength of the radiation 1,1a,1": from fraction of nanometers (synchrotron light), through nanometers (X-Ray) to several hundreds of nanometers (UV, visible light), etc.

From this reason the grating constant d of the array structure (matrix) of the channel's openings 5b belongs to the analogous range between several and several hundreds of nanometers.

The closer is the diameter s of the channels 5 to the grating constant d of the structure of the channel's openings 5b (preferable s≈<d), the higher will be the transmissivity of the converter 4.

The application of the inclined with an angle β (FIG. 1) (against the electronoptical axis) or curved channels 5 can be advantageous when considering the optimal photon absorption and photo-electron conversion.

The form of the cross section of the channels 5 (e.g. circle, triangle, quadrat, hexagon, in general case polygon) does not have (similar to the channel's structure) a decisive influence on the function of the converter 4, but on its transmissivity only.

The length of the channels l, or more correct the parameter l/s, that decides about the gain of the photo-electron converters 4, belongs to the range: $1 \le l/s \le 10^4$.

The inclination angle β of the converter's channels referred to the electronoptical axis belongs in the realization examples of the invention to the angle range between 0° and 90°.

As presented in the schematic way in FIG. 1, the investigated by the invented "NOTEM" method object 2 consists of the pixels a, b, c and d, that differ from each other in the context of material or/and chemical composition or/and structure or/and state of matter or/and density, etc.

Depending on the physical-chemical mechanisms that result in the different absorption-and/or scattering cross sections of the object 2 penetrating electromagnetic radiation 1,1a,1", an intensity contrast in the transmission photon image occurs that these mechanisms reflects.

The mechanical-optical system O, that is situated between the radiation source S and the investigated object 2, allows the user to optimize its illumination/penetration with the electromagnetic radiation as well as in the geometrical sense: 1) tilt of the radiation direction 1,1a,1" or/and 2) angular distribution of the electromagnetic beams (e.g. convergent or divergent or collimated beam), as in the physical context: 3) spectrum (e.g. wide or monochromatic spectrum or combination of the single, filtered wavelengths) or/and 4) polarization (e.g. non-polarized, polarized elliptically/circularly or polarized linearly electromagnetic radiation).

The illumination/penetration of the investigated object 2 with the electromagnetic radiation 1 can be enriched by the application of additional radiations, e.g. 1a,1" with different wavelength, polarizations, inclination angle, etc., that selectively excite the single chemical component and/or physical-chemical processes and therefore enhance the material contrast in the image ABCD.

The photons 1' of the transmission photon image ABCD of the illuminated by the electromagnetic radiation 1,1a,1" object 2 penetrate the closed ends (bottoms) 5a of the converter's channels 5 or/and the layer 3 or layers: 3a, 3b, 3c, etc. and occur on the vacuum side as a A'B'C'D' photon image at the photoemissive surface of the bottoms 5a of the channels 5.

Therefore it is essential, that the transmission process of the photons 1' through the closed ends (bottoms) 5a or/and the layer 3 or layers: 3a, 3b, 3c is homogenous (i.e. does not falsify the 2D information included in the photon's distribution ABCD) and the relationship between this photon's distribution ABCD and the transmission image A'B'C'D' exhibits a scalar-like, linear character.

The configuration of the channel's 5 closed ends (bottoms) 5a, and/or the layer 3 layers 3a, 3b, 3c (e.g. referred to their structure or chemical composition) results in the formulation of several examples of realization.

Taking the most basic realization as our example, the array of the closed channel's 5 ends 5a of the photon-electron convertor 4 establish per se a continuous and tight separation and photoemissive layer 3.

It is preferable on the one hand that the separation layer 3 (in this particular case ends/bottoms 5a) should be as thin as possible (implied by the condition of high photon's 1' transmissivity through this layer/photoemissive surface 5a into vacuum and the favored near-field regime), while on the other hand being mechanically stable/vacuum-tight and additionally assuring a high photoelectron emission coefficient.

Depending on the applied material, the thickness of the layer 3 (the closed channel's 5 ends 5a) measures from a few to a few hundreds of nanometers.

This value, besides the wavelength of the electromagnetic radiation 1,1a,1", relates to the Fresnel's diffraction limit, which in turn determines the lateral resolution: ≈, where λ means the wavelength and g the thickness of the layer 3 (closed channel's 4 ends 5a).

In the case of object's 2 illumination/penetration with the UV light 1,1a,1" with a wavelength of ~200 nm (~6.2 eV) and the thickness of the separation layer 3 amounts to 20 nm, the expected lateral resolution in the optical transmission image A'B'C'D' in the NOTEM microscope according to the invention equals to ~60 nm, whereat the material of the surface 5a exhibits a smaller than 6.2 eV work function to enable the photoelectric effect.

It should be indicated that this example of realization permits also the application of all other arbitrary electromagnetic radiations with the photon's energy $h\gamma > \phi$ (where $\phi$ means the work function of the material 16 of the channel 5 or/and its layer 17 or/and surface 3/3a): e.g. the application of the soft X-ray radiation 1,1a,1" with λ=10 nm results in the significant improvement of the lateral resolution in the optical transmission image A'B'C'D' from 60 nm (for UV light) to 14 nm, however, the longer in vivo observation of biological material is not available in this case.

Due to the fact that the lateral resolution of the cathode lens objective amounts to ~5 nm only, the total resolution of the invention's subject: NOTEM microscope equals to ~15 nm.

The similar channel's 5 separation (15 nm) has to be premised, however.

As mentioned earlier, the photons 1' of the electromagnetic radiation that penetrates the closed channel 5 ends (bottoms) 5a or and the layer 3 or layers 3a, 3b, 3c evoke in the photoemissive surface the photoelectric effect if the closed channel 5 ends (bottoms) 5a or and the layer 3 or layers 3a, 3b, 3c exhibit a sufficiently low work function: $\phi < h\gamma$.

If this is not the case, the channel's 5 surface will be covered (evaporated, from volume segregated, etc.) with the emissive layer 17, to which an electrostatic potential (e.g. ground potential) can be applied directly or by means of the contact electrode 18.

The vacuum chamber 20 having a vacuum connection 24 for pumping down, will be preferably equipped with one or more evaporators (molecular sources) 22, 23 and/or preferably with the gas inlet 25 for the in situ photo-activation of the surface 5a or/and 17. In an additional realization of the subject of invention (NOTEM microscope), the photo-activation of the channel's 5 surface 5a or/and 17 of the converter 4 will be carried out before the insertion of the converter 4 into the vacuum chamber 20.

Many different kinds of photocathodes and photoemissive substances known from other applications are available and depending on the radiation's 1,1a,1" wavelength (i.e. photon's energy) can be implemented into the photon-electron converter 4, for example: metallic substances (e.g. alkali metal), semiconductors, antimonides and halides of the alkali or alkaline-earth metals, ceramics, dotted substances, etc., In these particular cases the photoemissive substance can be also segregated onto the channel's 5 surface from the volume of the converter's material 16.

According to the invention, the channels 5 are one-way closed with the photoemissive layer 3a that on the vacuum side 20a the photoelectrons emits, otherwise their walls that are prepared from the material 16 with the secondary emission coefficient >1 (or/and are covered by the layer 17 with the secondary emission coefficient >1), which assures the high secondary electron yield from the array of channels 5.

In the case of the soft, low energy radiation 1,1a,1", e.g. UV light with the wavelength of λ=350 nm and the photon energy of hγ=3.5 eV (harmless for in vivo imaged biological objects), the work function of the vacuum exposed photoemissive surface of the closed ends (bottoms) 5a of the channels 5 is smaller than the photon energy: $\phi < 3.5$ eV.

This assumption resulting in the photoemission of electrons (in respect to the work function) will be satisfied e.g. by the alkali metals: for example cesium with the very low work function of 2.1 eV.

The essence of the invention of the "NOTEM" microscope is determined by the integration of the multi-channel photon-electron converter 4 with the cathode lens objective 8,9,9',9" and by the fact that the array (matrix) of the open ends (bottoms) 5b of the converter's 4 channels 5 is exposed in vacuum as an intermediate object of the cathode lens objective 8,9,9',9" in its object plane (a higher extractor field of the objective results in the deeper field penetration of the equipotential lines 7 into the channel's interior and the enhancement of the lateral resolution.

FIG. 1 illustrates the mechanism of the penetration of the equipotential lines 7 of the extractor field into the interior of the channels 5 and creation there of the potential gradient necessary for the successive acceleration of the secondary electrons 13 to the channel's openings 5b.

In the first stage the fraction of the electrostatic extractor field 7 inside the channel accelerates and directs to the extractor 8 the photoelectrons, which are primarily generated as a result of the photoelectric effect caused by the photon 1' absorption in the photoemissive converter's 4 material 16 in the closed ends (bottoms) 5a of the channels 5 and/or in the photoemissive layer 17 and/or photoemissive layer 3a on the vacuum side.

The collisions of the photoelectrons with the channel's wall and the subsequent "downwelling" emission of the secondary electrons are promoted by the sub-micrometers channel 5 diameter (preferably from ~1 nm to ~$10^3$ nm).

In the example realization according to the invention, the converter's 4 body is preferably made of a material 16 with the secondary emission coefficient >1 and/or the channel's 5 walls are covered by the evaporated (or PVD, CVD, etc.) or from the volume of the converter's body segregated material 16 with secondary emission coefficient >1.

If the channel's length (compared to the channel's diameter) is large enough, i.e. l/d≤1, the extractor field inside the channel (as a result of an applied voltage in the channel's interior) accelerates the secondary electron cloud 13 to the next collision with the surface of the channel's wall 17.

This "downwelling" process continues till the secondary electrons 13 leave the channels 5 towards the extractor 8 through the array (matrix) of the channel's openings 5b situated in the object plane of the cathode lens objective 8,9,9',9".

In FIG. 1, for the purpose of clarity, one collision with the photoemissive layer 17 of the channel's wall has been indicated.

In the example realization according to the invention, the convertor's channels operate also (besides the stimulation of the electron processes) as an array of optical waveguides for photons 1' of the electromagnetic radiation 1,1a,1", in which continuing photoelectric processes and multiplied generation of photoelectrons takes place.

As a consequence of the above-mentioned processes, the two dimensional intensity distribution of all secondary electrons 13 at the output from the array (matrix) of the channel 5 openings 5b in all example realization taking of the invented microscope is correlated to the optical image contrast ABCD resulting from the transmission of the object 2 penetrating electromagnetic radiation 1,1a,1" (in the optical part of the Near-field Optical Transmission Electron Emission Microscope) and becomes an intermediate (electron) object of the cathode lens objective 8,9,9',9" (in the electronoptical part of the Near-field Optical Transmission Electron Emission Microscope).

This electron intermediate object will subsequently be magnified by the cathode lens objective 8,9,9',9" and/or by the adjacent electronoptical system 21 and as an electron image at the image detector recorded: at the image amplifier 14 (e.g. 2D delay line detector) and/or screen (fluorescent or e.g. YAG crystal etc.)

In the example realization of the Near-field Optical Transmission Electron Emission Microscope its lateral resolution will be improved by the insertion of the fixed or exchangeable contrast aperture 10 and/or a stigmator 11 in the diffraction (focal) plane of the cathode lens objective 8,9, 9',9" and/or in one of the correlated planes.

The electronoptical part of the NOTEM microscope in which the electrons propagate (starting from the bottoms 5a of the converter's channels 5 and/or from the layer 3/3a and/or layer 17 to the image detector 14,15) is arranged under vacuum 20a in the interior of the vacuum chamber 20.

In the case of the necessity (or usefulness) of a protective separation (mechanical and/or chemical) between the investigated object 2 and emissive layers 3a/3b, an additional (several to several hundred nm thick) contact buffer layer 3c (e.g. $SiO_2$ or $Si_3N_4$, etc., preferably transparent for electromagnetic radiation 1,1a,1") will be incorporated onto the top of converter 4, assuring its direct mechanical and/or optical coupling to the investigated object 2.

As an enrichment of the previous variants of the realization examples, the integrated with the photon-electron converter 4 object of investigation 2 can be modified in real time during the observation (or before) by: mechanical and/or chemical and/or physical and/or electrochemical and/or electrical and/or magnetic, etc. processes realized by the application of one or several manipulators 2' and/or generators for the object's modifications.

In the second group of the realization examples of NOTEM microscope that relates to all the earlier practical aspects, the photon-electron converter 4 is hermetically (vacuum tight) coupled with its array (matrix) of the opened ends 5b of the converter's channels 5 to the vacuum chamber 20, preferably in such a way that the object shift and/or tilt/adjustment (with respect to the electronoptical axis of the cathode lens objective 8,9,9',9") is assured, e.g. by the implementation of the element 6 as a converter 4 holder and the bellow 12 that is hermetically coupled to this element 6 as well as to the vacuum chamber 20.

Such a vacuum-tight flexible separation allows the electron imaging and the selection of an arbitrary area of the investigated objects outside the vacuum.

The third example realization of the invented Near-field Optical Transmission Electron Emission Microscope "NOTEM" enables the object observation under vacuum (or in the arbitrary gas atmosphere).

In this example the investigated object 2 will be encapsulated in the hermetic chamber 26 equipped with a transparent window (for the external source S electromagnetic radiation 1,1a,1") and additionally with the vacuum port 28 for pumping down and/or with the inlet port 29 for the selective gas dosage under an arbitrary pressure.

Therefore in this example realization it is possible to expose the investigated object 2 to any vacuum assisted processes, e.g. plasma discharge, evaporation, (PA)PVD, CVD, (PA)CVD, etc. in real time during the observation or before.

The fourth example of realization differs from the previous in the establishing of the internal vacuum connection between the two vacuum chambers 20 and 26 (in this particular case they built a single, common chamber).

Depending on the vacuum connection, differential pumping can be used for pressure regulation.

Three further realization examples of the invented NOTEM microscope introduce to the previous realization aspects variations in the kind and character of the converter's body material 16, which facilitates the creation of the sub-micrometric channel's (capillaries) structure and belongs to the following classes: insulators, e.g. ceramics: $Al_2O_3, CaF_2, MgO, Si_3O_4, SiO_2, ZrO_2, Cr_2O_3, BaTiO_3$, etc., in the realization example 5 and/or semiconductors in the realization example 6 and/or conductors in realization example 7.

The following realization example extends all the previously described practical aspects by the procedure (described below) for the additional enhancement of the electrostatic field 7 which naturally develops in the channel's interiors 5 as a result of the successive extractor 8 field penetration 7 (established by the electronoptical integration of the photon-electron converter 4 with the cathode lens objective 8,9,9',9'').

This additional procedure is particularly important for photon-electron converters with l/d>~1, when the further extractor field penetration in the channel's interiors is handicapped by the screening action of the channel's walls.

In the invented Near-field Optical Transmission Electron Emission Microscope "NOTEM" the effect of the electrostatic field enhancement in the channel's interiors 5 of the converter 4 will be generated by the applying of the voltage between the bottoms (closed ends) 5a of the convertor's channels 5 (and/or the layer 3/3a) and the frontal face of the array (matrix) of the opened channel ends 5b (i.e. across the converter), either directly, or with the contact electrodes: 3b and 18, respectively.

The vacuum exposed surface of the channels' closed ends (bottoms) 5a and/or layer 3a (from several to several hundred nanometers thick) operates as a photocathode illuminated from the object side by the photons 1' of the object 2 penetrating electromagnetic radiation 1,1a,1''.

In a particular case, they form with a contact electrode 3b a single, common layer, i.e. the layer 3a and/or the channel's 5 closed ends (bottoms) 5a of the converter 4 operate as well as a photocathode and as a contact electrode.

Also in this example realization the necessity (or usefulness) of a protective separation (mechanical and/or chemical) between the investigated object 2 and emissive layers 3a/3b can be considered, as an additional (several to several hundred nm thick) contact buffer layer 3c (e.g. $SiO_2$ or $Si_3N_4$, etc., preferably transparent for electromagnetic radiation 1,1a,1'') that will be incorporated onto the top of the converter 4, assuring its direct mechanical and/or optical coupling to the investigated object 2.

In the described realization example of the invented Near-field Optical Transmission Electron Emission Microscope "NOTEM", the interior of the converter's channels 5 will be covered by the properly aligned (modeled) resistive layer 17 with the secondary electron emission coefficient>1, by means of evaporation, segregation from converter's body material, plasma discharge, etc., whereby together with the contact electrodes 3b (or/and layer 3a or/and 5a) and 18 the closed electrical circuit will be formed.

The current flow, resulting from the applied (as a "minus" to the contact electrode 3b (and/or to layer 3a or/and 5a) and as a "plus" to the contact electrode 18) voltage, generates in the resistive layer 17 of the converter's channels' 5 interior a linear voltage drop and thereby an additional (besides the penetrating electrostatic field) component of the accelerating field $\sim U/I$ (U—applied voltage, I—channel's length) that exhibits an advantageous influence on the secondary electron yield (and subsequently on the intensity of the secondary electron image (intermediate object) 13 at the output from the array (matrix) of the channel's openings 5b in the object plane of the objective 8,9,9',9'') as an effect of the successive, downwelling electron collisions with the emissive channel's surface 17.

Some other more detailed realization examples of the NOTEM microscope can be derived from the above general description considering the plurality of the following aspects: 1)the character and form of the object penetrating electromagnetic radiation 1,1a,1'', 2)the structure, geometry, chemical composition and channel's form and structure, 3)the character of the electronoptical system.

As a cathode lens-based apparatus, the Near-field Optical Transmission Electron Emission Microscope "NOTEM" makes use of available cathode lens objective types: electrostatic and/or magnetic, e.g. Diode, Triode, Tetrode, Pentode, etc.

Figure 2A:
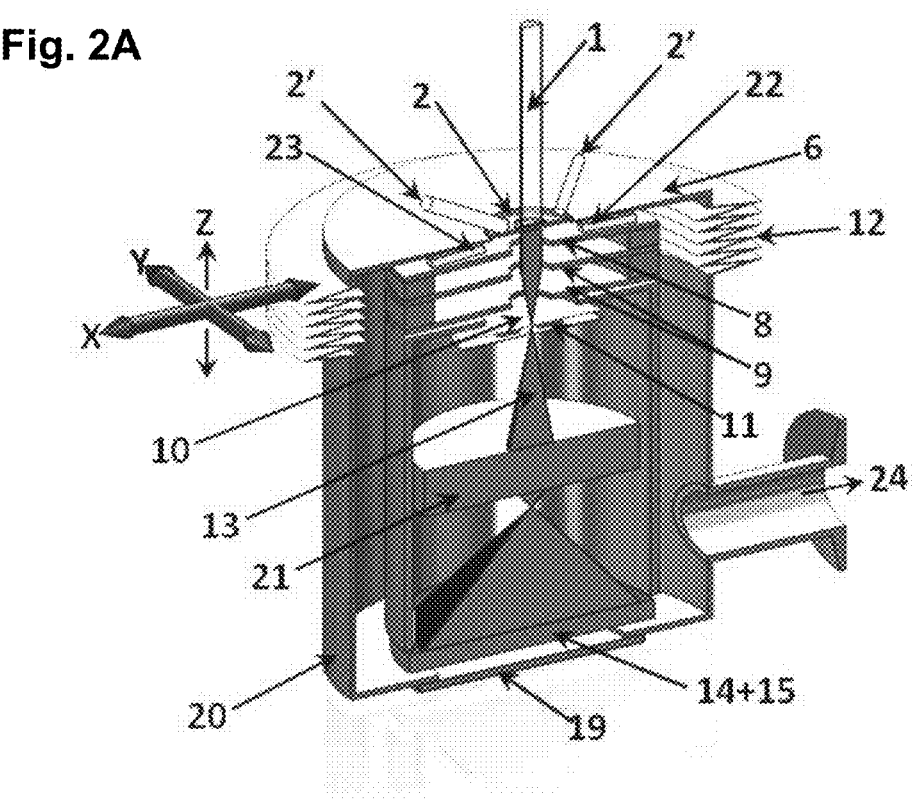
FIG. 2A presents the subject of invention (as a cross section not to scale-drawing) in the first selected example of realization, in which the investigated object situated outside the vacuum that appears in an arbitrary state of matter, will be integrated with the photon-electron multichannel converter/object holder, the cathode lens objective focuses electrostatically and the non-polarized or polarized linearly or elliptically (circularly) electromagnetic radiation illuminates/penetrates the investigated object and enters the converter's channels under an arbitrary angle inducing there the photoelectric effect.
Figure 2B:
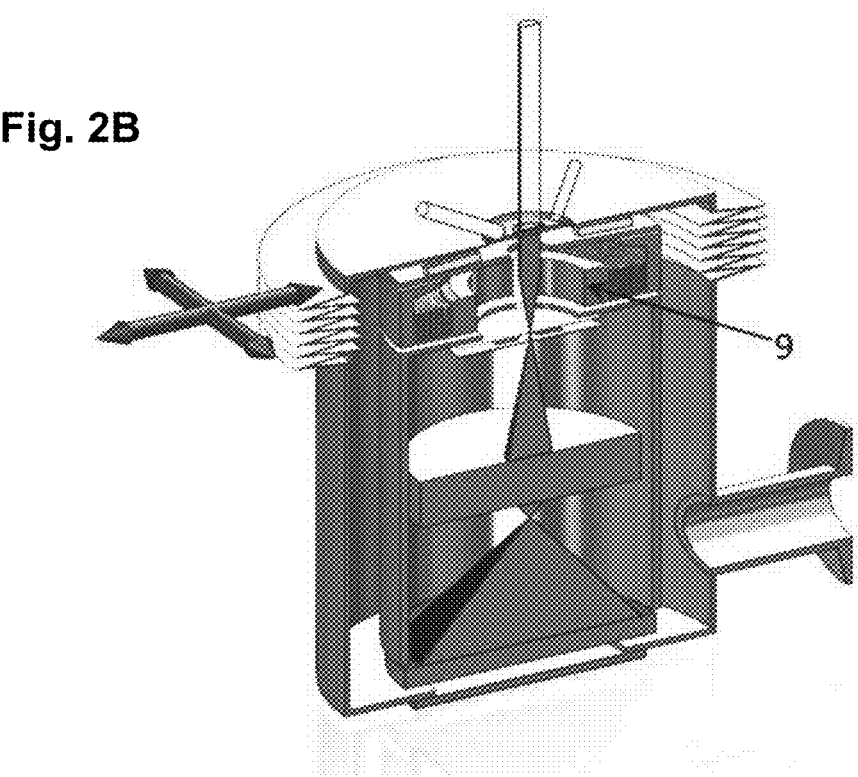
FIG. 2B corresponds to FIG. 2A except that the cathode lens objective focuses magnetically instead of electrostatically.

FIGS. 2A and 2B illustrate the "NOTEM" microscope in the two chosen example realization taking relating to the nature of the employed cathode lens objective 8,9: the electrostatic Tetrode 8,9'—FIG. 2A and the magnetic Triode 8,9''—FIG. 2B.

These realization examples has been derived from the general instrumental outlook in FIG. 1 and include all mentioned aspects and variants of the solution in the context of: e.g. photon-electron converter 4, the object penetrating radiation 1,1a,1'', the electronoptics, construction or electron image detector, etc.

All the electronoptical elements and lenses presented in the FIGS. 2A and 2B are encapsulated in the vacuum chamber 20: 1)the array (matrix) of the channel openings 5a of the converter 5 (as an object/cathode of the cathode lens objective 8,9,9',9''') and the channels itself, 2)the cathode lens objective 8,9,9',9'', 3)the contrast aperture 10, 4)the stigmator 11, 5)the electronoptical system 21, 6)the electron-photon image detector 14,15 and 7) the electron trajectories.

Typically, the vacuum chamber 20 will be equipped inter alia with the following elements and functions: 1) connection vacuum flange 24 for pumping down, 2)vacuum tight, mechanical coupling between the converter 4 and the cathode lens objective 8,9,9',9'', e.g. by means of the converter holder 6, bellow 12 and object 4 manipulator XY (or/and Z or/and tilt), which enables the shift and/or adjustment of the converter/(object holder) 4 together with the attached investigated object 2.

Thereby the open access from the air side to the imaged object 2 will be assured, e.g. the possibility of the real time in situ manipulations or modifications with the micro-(sub-micron) manipulators 2' or application of different fluids (or gases) from the natural environment of the object 2 (or fluids as an autonomic investigation objects)

Apart from the connection vacuum flange 24 and object manipulator XY, the vacuum chamber is equipped with the viewport 19 for the observation of the magnified electron image at the fluorescent screen 15 and/or with the electrical vacuum feedthrough for the recording of the electron image with the electron detector 14 (e.g. 2D delay line detector).

The beams of the object penetrating electromagnetic radiation 1,1a,1'' will preferably be modeled by the mechanically-optical system O, which enables the geometrical adjustment (e.g. tilt and/or shift) with respect to the image center and/or modeling of the required physical properties (e.g. phase, spectrum, geometrical form, polarization, etc.).

Alongside the imaging (object penetrating) electromagnetic main—radiation 1 as in the previous example, the imaged object 2 can also be illuminated/penetrated by the accompanying radiation (or radiations) 1a,1'', e.g. with other wavelength in order to: 1) activate processes in the investigated object 2 and/or 2) excite chemical and/or physical (or structural) components and/or resonances and/or 3) enhance contrast and/or 4) modify chemical/structural composition, etc.

Referring to the above realization example, the NOTEM microscope will be further equipped with the second object manipulator 2', which enables micro-(or sub-micro) manipulations inside the imaged object 2, e.g. in the case of biological objects: 1) localized, selective dosage of the chemical substances targeted to individual chosen cells or cell nucleus, 2) implementation into the investigated object 2 of an impulse generating (or impulse recording) miniature electrode for real time observations, etc.

A further example realization enables the investigated object to be exposed to the magnetic and/or electric field.

The Near-field Optical Transmission Electron Emission Microscope "NOTEM" will be equipped in subsequent example realizations with other standard arbitrary measurement instrumentation, e.g.: AFM, MFM, EFM, KPFM, etc. (atomic-, magnetic-, electric-, Kelvin probe-force microscopy) and/or with the classical optical microscope (for simultaneous or successive observations).

All of these external instruments will preferably be mounted on to the moveable platform or coupled in such a way to the NOTEM microscope that the electromagnetic radiation 1,1a,1" will not be blocked.

The realization example in FIG. 2B differs from that in FIG. 2A in the application of the magnetic cathode lens objective (Triode) 8,9" instead the previous electrostatic one.

Similarly, at this stage any arbitrary type of magnetic cathode lens objective can be used, e.g. a magnetic Tetrode.

All the earlier realization examples related to the FIGS. 2A and 2B will be enriched by the introduction of the hermetic vacuum chamber 26 that is vacuum tight connected to the top (element 6) of the vacuum chamber 20 and can be evacuated (pumped down) through the connecting vacuum flange 28 establishing the vacuum around the investigated object 2.

Such an instrumental extension opens the access to the wide area of the material engineering, e.g. Thin Film Technology and enables the in situ object preparation and/or in situ object modification with e.g. epitaxy, lithography, catalysis, diffusion, adsorption, desorption, segregation, corrosion, ion implementation, doping, glowing in gases, plasma technologies, etc., during the object observation (real time parallel imaging), as well as in the preparation phase.

The vacuum chamber 26 will be equipped with object oriented connecting flanges that enable not only the adaptation of the external standard methods, but also the detection of the object signals (e.g. reflected photons).

In the further realization example an arbitrary gas atmosphere under arbitrary pressure (also overpressure) will be generated around the investigated object 2 by means of the gas inlet flange 29, whereby it will be possible to carry out real time imaging of physical/chemical reactions and processes in the investigated object 2 in an arbitrary state of matter.

The source S of the object penetrating electromagnetic radiation 1,1a,1" is situated either inside the vacuum chamber 26 or outside: the radiation penetrates the investigated object through a suitable vacuum tight window 27, e.g. beryllium window in the case of X-Ray or quartz window in the case of UV light.

Figure 3A:
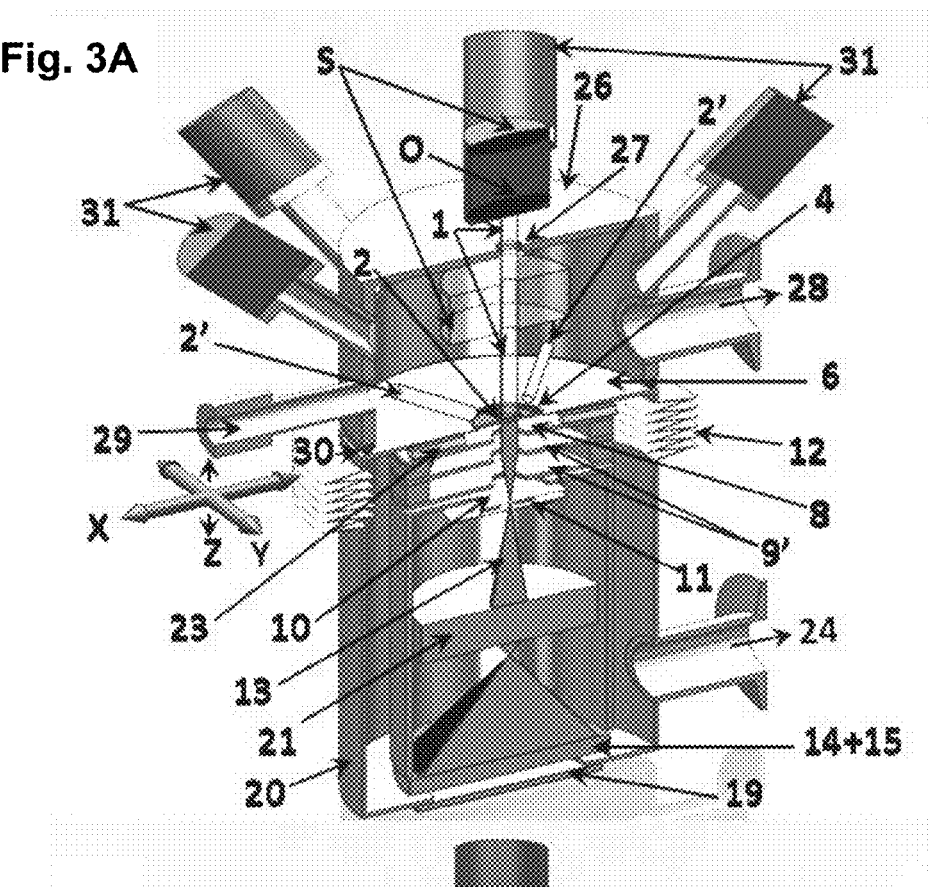
FIG. 3A presents the subject of invention (as a cross section drawing-not to scale) in the second selected example of realization, in which: 1) the investigated object in an arbitrary state of matter, integrated with the photon-electron multichannel converter/object holder is encapsulated in the independent hermetic chamber (for the pumping down and/or filling with arbitrary fluids and/or arbitrary gases or gas mixture under an arbitrary pressure), 2) the cathode lens objective focuses electrostatically and 3) the non-polarized or polarized linearly or elliptically (circularly) electromagnetic radiation illuminates/penetrates the investigated object and enters the converter's channels under an arbitrary angle inducing there the photoelectric effect.
Figure 3B:
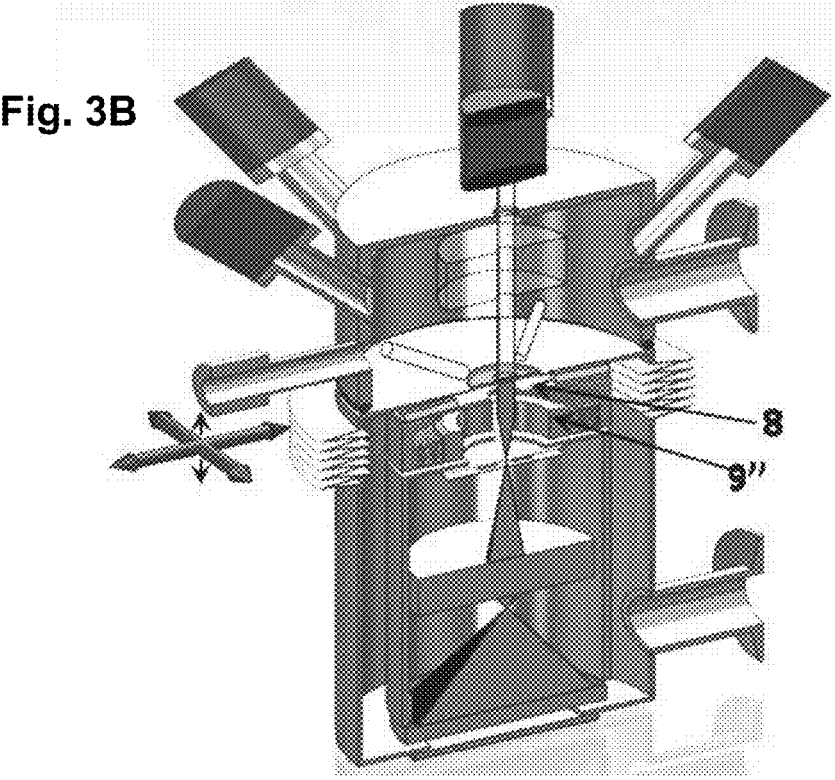
FIG. 3B corresponds to FIG. 3A except that the cathode lens objective focuses magnetically instead of electrostatically.

Referring to the above realization example in FIGS. 3A and 3B, the NOTEM microscope will be further equipped with the second object manipulator 2', that enables micro-(or sub-micro) manipulations inside the imaged object 2, e.g. in case of biological objects: 1) localized, selective dosage of the chemical substances targeted to individual chosen cells or cell nucleus, 2) implementation into the investigated object 2 of an impulse generating (or impulse recording) miniature electrode for real time observations, etc.

A further realization example enables the investigated object to be exposed to the magnetic and/or electric field.

The Near-field Optical Transmission Electron Emission Microscope "NOTEM" in the realization example in FIGS. 3A and 3B can be equipped in later realization examples with the other standard arbitrary measurement instrumentation, e.g.: SEM, STM, AFM, MFM, EFM, KPFM, etc. (scanning, atomic-, magnetic-, electric-, Kelvin probe-force microscopy) and/or with the classical optical microscope (for simultaneous or successive observations).

All of these external instruments will preferably be mounted on to the moveable platform or coupled in such a way to the NOTEM microscope that the electromagnetic radiation 1,1a,1" will not be blocked.

The realization example in FIG. 3B differs from that in FIG. 3A in the application of the magnetic cathode lens objective (Triode) 8,9" instead of the previous electrostatic one.

At this stage any arbitrary type of magnetic cathode lens objective can be used, e.g. a magnetic Tetrode.

In the further realization example related to the variant with electrostatic (FIG. 3A) as well as magnetic cathode lens objective (FIG. 3A) the two vacuum chambers 20 and 26 are internally connected-in this particular case they built a single, common area for the investigated object 2 as well as the electrons 13.

Depending on the vacuum connection, differential pumping can be used for the pressure regulation.

LIST OF REFERENCE NUMERALS 1. object penetrating/illuminating electromagnetic radiation
1a. additional object penetrating/illuminating electromagnetic radiation
1'. photons of the electromagnetic radiation (1) after transmission through the imaged object
1". object penetrating/illuminating electromagnetic radiation inclined under an angle $0° \leq \alpha \leq 90°$
2. object of imaging
2'. manipulator for the modification of the object (2)
3. layer or multilayer that closes at one side the channels (5)
3a. layer forming the photoemissive bottom (5)
3b. transparent contact electrode that feeds the potential to the bases of the channels (5)
3c. transparent separation-and/or protective layer of the investigated object (2)
4. photon-electron converter/object (2) holder
5. channels of the converter (4)
5a. closed end (bottom) of the channel (5)
5b. array (matrix) of the channel's openings (5)
6. hermetic holder of the converter (4): component of the object (2) manipulator—e.g. X, Y, Z, ⊖
7. equipotential lines of the electrostatic field of the cathode lens objective
8. extractor of the cathode lens objective
9. electronoptical element of the cathode lens objective for the electrostatic and/or magnetic focusing
9'. electronoptical element of the cathode lens objective for the electrostatic focusing
9". electronoptical element of the cathode lens objective for the magnetic focusing 10. contrast aperture
11. Stigmator
12. flexible bellow connection for the e.g. X, Y, Z, ⊖ shift/adjustment of the imaged object (2) and together with its converter/object holder
13. secondary electrons generated in convertor's channels 5
14. electron image detector
15. screen
16. converter's material
17. upper layer in the converter's channels with secondary electron emission coefficient >1
18. contact electrode defining the potential of the opening's array (matrix) (5b) of the converter (4)
19. vacuum viewport
20. hermetic vacuum chamber
20a. vacuum
21. electronoptical system
22. molecular source for the activation of the surfaces and/or evaporating of the convertor's channels (5)
23. additional molecular source
24. connecting flange used for pumping down of the vacuum chamber (20)
25. connecting flange used for the gas inlet (under arbitrary pressure and composition)
26. additional hermetic chamber (housing) of the investigated object (2)
27. transparent for the electromagnetic radiation (1,1a,1") vacuum window
28. connecting flange used for pumping down of the vacuum chamber (26)
29. connecting flange in the hermetic object (2) chamber (housing) used for the gas inlet (under arbitrary pressure and composition)
30. vacuum gasket used for the hermetic connection between the object (2) chamber (26) and vacuum chamber (20)
31. access port to the investigated object (2)
S sources of the electromagnetic radiation (1,1a,1")
O mechanical/optical system for the forming of radiation with respect to: geometry, phase, spectrum, etc.
α a inclination incident angle of the radiation (1,1a,1")
β tilt angle of the channels (5) related to the electronoptical axis
abcd chemical/physical structure of the investigated object (2)
ABCD optical transmission image of the object's structure abcd
A'B'C'D' photoelectron image after conversion of the optical transmission image (ABCD) in the photoemissive surface of the channel's bottoms of the converter (4)
A"B"C"D" electron image generated by the secondary electrons (13) at the output from the channel's opening array (5b) in the object plane of the cathode lens objective (8,9,9',9")

The invention claimed is:
1. A Near-field Optical Transmission Electron Emission Microscope, comprising:
 a. an image magnifying electronoptical system containing a cathode lens objective and an electron image detector,
 b. a vacuum tight housing having at least one connecting port for pumping,
 c. at least one object penetrating electromagnetic radiation and
 d. an object holder for the investigated object
wherein
 the object holder (4) of investigated object (2) is arranged between the investigated object (2) and the image magnifying electronoptical system,
 the object (2) holder (4) comprises channels (5), that are closed on the side of the investigated object (2) by the bottoms (5a) creating one common layer (3), on which the investigated object (2) overlies, and the channels are opened on the side of the electronoptical system and that are formed as a photon-electron-converter (4) for the proportional conversion of the photons of the optical transmission image (1') of the investigated object (2) to photoelectrons,
 the channels (5) form an array of openings (5b) on the opposite side of the object (2) holder (4) in the object plane of the cathode lens objective (8,9,9',9"),
 the channels (5) of the object (2) holder (4) are suited in means of an emissive surface to generate the secondary electrons (13) proportional to the intensity of photoelectrons,
 the electronoptical system containing the cathode lens objective (8,9,9',9") generates the magnified electron image of the investigated object (2) at the electron image detector (14).
2. The Near-field Optical Transmission Electron Emission Microscope according to claim 1, wherein the photon-electron-converter (4) has a first contact electrode (18) in vacuum (20a) at the open ends (5b) of the channels (5) and a second contact electrode (3b/3a) at the bottom (5a) of the channels (5) on the side of investigated object (2), whereat the inner walls of the channels (5) are covered by a resistive layer (17) connecting the said electrodes (18) and (3b/3a) and the accelerating potential inside the channels (5) is generated by applying of a higher electrical potential to the first contact electrode (18) and the lower electrical potential to the second contact electrode (3b/3a), and the photon-electron-converter (4) is applicable as a secondary electron multiplier.
3. The Near-field Optical Transmission Electron Emission Microscope according to claim 2, wherein the secondary electrons from the two dimensional array of the open ends (5b) of the channels (5) of the converter (4) are emitted in the object plane of the cathode lens objective (8,9,9',9") as a secondary electron object of the further electronoptical imaging, that is correlated with the optical transmission image (1') of the investigated object (2) and magnified with the electronoptical system containing the cathode lens objective (8,9,9',9") at the electron image detector (14).
4. The Near-field Optical Transmission Electron Emission Microscope according to claim 1, wherein the material of the walls (16) of the channels (5) of the converter (4) is identical with the material of the bottoms (5a) of the channels (4).
5. The Near-field Optical Transmission Electron Emission Microscope according to claim 1, wherein the walls (16) of the channels (5) of the converter (4) and/or the bottoms (Sa) of the channels (5) consist of an insulator and/or conductor and/or semiconductor.
6. The Near-field Optical Transmission Electron Emission Microscope according to claim 1, wherein the surface of the bottoms (5a) of the channels (5) of the converter (4) is photoemissively responsive to the photons (1') of the object penetrating electromagnetic radiation (1,1a,1") and the surface of the inner walls of the channels (5) of the converter (4) has a secondary electron emission coefficient larger than one.
7. The Near-field Optical Transmission Electron Emission Microscope according to claim 1, wherein the photon-electron-converter (4) is hermetically coupled with the side of the opened ends (5*b*) of the channels (5) in the direction of the cathode lens objective (8,9,9',9") to the vacuum housing (20) and separates the vacuum (20*a*) generated in the vacuum housing (20) from the investigated object (2).

8. The Near-field Optical Transmission Electron Emission Microscope according to claim 7, wherein the second hermetic housing (26) that separates the investigated object (2) from the ambient atmosphere is vacuum tight connected to the vacuum housing (20) and equipped with at least one connecting port (28) and a transparent for the object (2) penetrating electromagnetic radiation (1,1*a*,1") vacuum tight window.

9. The Near-field Optical Transmission Electron Emission Microscope according to claim 8, wherein the hermetic housing (26) can be filled with a gas or fluid at an arbitrary pressure.

10. The Near-field Optical Transmission Electron Emission Microscope according to claim 1, wherein the photon-electron-converter (4) is coupled with the vacuum housing (20) via a hermetic bellow (32) in such a way that the photon-electron-converter (4) can be shifted and/or adjusted by means of the operating control that the array of the opened ends (S*b*) of the channels (5) of converter (4) remains in the abject plane of the cathode lens objective (8,9,9',9"), the imaged area of the array of the opened ends (5*b*) of the channels (5) will be changed however.

11. The Near-field Optical Transmission Electron Emission Microscope according to claim 1, wherein the Near-field Optical Transmission Electron Emission Microscope has one or more object (2) manipulators (2').

\* \* \* \* \*